United States Patent [19]

Bender et al.

[11] 3,931,232
[45] Jan. 6, 1976

[54] 3-ALKYL XANTHENE COMPOUNDS

[75] Inventors: Paul E. Bender, Willingboro, N.J.; Bernard Loev, Broomall, Pa.

[73] Assignee: SmithKline Corporation, Philadelphia, Pa.

[22] Filed: June 24, 1974

[21] Appl. No.: 482,049

[52] U.S. Cl. .............................................. 260/335
[51] Int. Cl.$^2$................ C07D 311/82; C07D 311/80
[58] Field of Search .................................... 260/335

[56] References Cited
OTHER PUBLICATIONS

Chazan et al., Bull. Soc. Chim. Fr., (1968) (4), pp. 1384–1393.

U. Claussen et al., Tetrahedron, Vol. 24, Apr. 1968, pp. 2897–2898.

*Primary Examiner*—Norma S. Milestone
*Attorney, Agent, or Firm*—Janice E. Williams; Alan D. Lourie; William H. Edgerton

[57] ABSTRACT

The compounds of this invention are 3-alkyl xanthenes having pharmacological activity such as central nervous system activity. Preferred compounds of this invention are 3-(1,2-dimethylheptyl)-5,6,7,8-tetrahydro-1-hydroxy-9-methylxanthene, 3-(1,2-dimethylheptyl)-1-hydroxy-6,9-dimethylxanthene and 3-(1,2-dimethylheptyl)-1-hydroxy-9-methylxanthene.

7 Claims, No Drawings

3-ALKYL XANTHENE COMPOUNDS

This invention relates to new 3-alkyl xanthenes which have pharmacological activity.

The compounds of this invention are represented by the following structural formula:

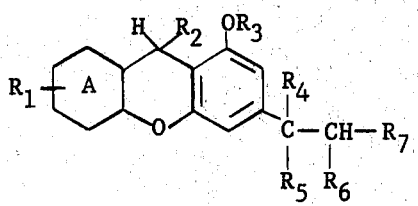

FORMULA I in which:
ring A is a benzene ring, a cyclohexane ring or a cyclohexene ring with the double bond at position 5a–8a;
$R_1$ is hydrogen, methyl or ethyl;
$R_2$ is hydrogen, methyl or ethyl;
$R_3$ is hydrogen or alkanoyl of from two to five carbon atoms;
$R_4$ is hydrogen, methyl or ethyl and $R_5$ and $R_6$ are hydrogen or methyl, at least one of $R_4$, $R_5$ and $R_6$ being other than hydrogen; and
$R_7$ is alkyl of from four to eight carbon atoms.

In the nomenclature used herein the xanthene ring is numbered as follows:

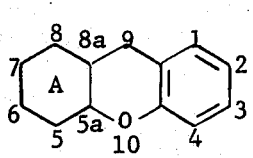

Preferred compounds of this invention are represented by Formula I in which ring A is a benzene ring or a cyclohexene ring with the double bond at position 5a–8a. Most preferred are the compounds of Formula I in which ring A is a benzene ring or a cyclohexene ring with the double bond at position 5a–8a, $R_4$ is methyl and $R_5$ and $R_6$ are hydrogen or methyl.

Advantageous compounds of this invention are represented by Formula I in which ring A is a benzene ring or a cyclohexene ring with the double bond at position 5a–8a, $R_1$ is hydrogen or methyl in the 6-position, $R_2$ is hydrogen or methyl, $R_3$ is hydrogen or acetyl, $R_4$ is methyl, $R_5$ and $R_6$ are hydrogen or methyl and $R_7$ is n-pentyl.

Particularly preferred are the compounds 3-(1,2-dimethylheptyl)-5,6,7,8,-tetrahydro-1-hydroxy-9-methylxanthene, 3-(1,2-dimethylheptyl)-1-hydroxy-6,9-dimethylxanthene and 3-(1,2-dimethylheptyl)-1-hydroxy-9-methylxanthene.

The compounds of this invention may exist as optical isomers due to the asymmetry of carbon atoms in the side chain, in ring A and at position 9 of the xanthene system. All of the isomers, including separated isomers and mixtures thereof, are included within the scope of this invention.

The compounds of Formula I in which ring A is a benzene ring or a cyclohexene ring with the double bond at position 5a–8a and $R_3$ is hydrogen are prepared by heating the product formed from condensation of a 2-formyl, 2-acetyl or 2-propionyl cyclohexanone with a 5-alkyl resorcinol in acid solution, for example in acetic acid containing hydrogen chloride. When a mixture of tetrahydro and aromatic products is formed, it is separated by standard methods such as column chromatography and fractional distillation.

The compounds of Formula I in which ring A is a cyclohexene ring with the double bond at position 5a–8a and $R_3$ is hydrogen are also prepared by treating the condensation product of a 2-formyl, 2-acetyl or 2-propionyl cyclohexanone and a 5-alkyl resorcinol, formed as described above, with a metal hydride such as sodium cyanoborohydride or a reducing metal such as zinc. To facilitate separation of the reaction products, the mixture is preferably acetylated by standard methods such as reaction with acetic anhydride or acetyl chloride, chromatographed and the product 1-acetoxy-3-alkyl-5,6,7,8-tetrahydroxanthene then hydrolyzed, for example with potassium carbonate in aqueous alcohol, to the corresponding 1-hydroxy compound of Formula I.

When ring A is a benzene ring and $R_3$ is hydrogen, the corresponding compounds of Formula I are also prepared by dehydrogenation of the compounds in which ring A is a cyclohexene ring. The dehydrogenation is carried out either using a chemical dehydrogenating agent such as 2,3-dichloro-5,6-dicyanoquinone or using a catalyst such as palladium-on-carbon.

The 3-alkyl-5a,5,6,7,8,8a-hexahydro-1-hydroxyxanthenes of Formula I, in which ring A is a cyclohexane ring and $R_3$ is hydrogen, are prepared from the corresponding compounds in which ring A is a cyclohexene ring by chemical or catalytic reduction according to standard procedures such as with platinum on silica gel in acetic acid.

The compounds of Formula I in which $R_3$ is lower alkanoyl are prepared from the corresponding compounds in which $R_3$ is hydrogen by conventional methods, for example by reacting the hydroxy compound with a lower alkanoic acid in the presence of a dehydrating agent such as dicyclohexylcarbodiimide, a lower alkanoic acid anhydride or a lower alkanoyl halide.

The alkyl substituted resorcinols are prepared from reaction of 3,5-dimethoxyacetophenone, 3,5-dimethoxybenzaldehyde or 3,5-dimethoxybenzonitrile with an appropriate alkyl magnesium halide with subsequent dehydration of the intermediate alcohols followed by hydrogenation and removal of the protective groups by standard procedures, for example by acid hydrolysis or with pyridine hydrochloride or boron tribromide.

The compounds of this invention have pharmacological activity such as central nervous system activity; for example the compounds have central nervous system depressant, sedative and tranquilizing activity. In addition, the compounds may have analgesic, gastric acid secretion inhibitory, anti-convulsant and anti-arthritic activity.

The central nervous system activity is demonstrated by oral administration to rats at doses of about 10 to 100 mg./kg. to produce effects such as decreased spontaneous motor activity.

One skilled in the art will recognize that in determining the amounts of the compound to produce the desired pharmacological effect, the activity of the compound as well as the size of the host animal must be considered.

The compounds of this invention may be combined with standard pharmaceutical carriers and administered internally in conventional dosage forms such as capsules, tablets or liquid preparations.

The following examples illustrate the invention but are not to be construed as limiting the scope thereof. Temperatures are in degrees Centigrade unless otherwise stated.

EXAMPLE 1

3-(1,2-Dimethylheptyl)-5,6,7,8,-tetrahydro-1-hydroxy-6,9-dimethylxanthene

A solution of 3.6 g. of 2-acetyl-5-methylcyclohexanone and 5.6 g. of 5-(1,2-dimethylheptyl)resorcinol in 150 ml. of acetic acid is cooled to 15° and saturated with hydrogen chloride gas. The solution is allowed to warm to 25°, stirred for 20 hours and then heated for one hour on a steam bath. The reaction mixture is concentrated in vacuo, water is added and the residue is dissolved in ethyl acetate. The ethyl acetate solution is washed with water, dried ($MgSO_4$) and concentrated to give a residue which is distilled five times, b.p. 195°–200° (0.025 mm.). The distillate is chromatographed on silica gel with benzene as eluant. The second fraction is collected and distilled to give the title compound, b.p. 190°–195° (0.05 mm.).

EXAMPLE 2

3-(1,2-Dimethylheptyl)-1-hydroxy-6,9-dimethylxanthene

A solution of 1.7 g. of 3-(1,2-dimethylheptyl)-5,6,7,8-tetrahydro-1-hydroxy-6,9-dimethylxanthene in 70 ml. of p-cymene is added dropwise over one hour to a stirred suspension of 0.56 g. of 10% palladium-on-carbon in 70 ml. of refluxing p-cymene under a nitrogen atmosphere. The reaction mixture is refluxed for four hours, cooled and chloroform is added. The mixture is filtered and the filtrate is concentrated in vacuo to give a residue which is chromatographed on silica gel with 1:1 chloroform-cyclohexane as eluant to give the title compound, b.p. 208°–210° (0.004 mm.).

EXAMPLE 3

3-(1,2-Dimethylheptyl)-5,6,7,8-tetrahydro-1-hydroxy-9-methylxanthene and
3-(1,2-dimethylheptyl)-1-hydroxy-9-methylxanthene A. A solution of 2.48 g. of 2-acetylcyclohexanone and 4.17 g. of 5-(1,2-dimethylheptyl)resorcinol in 100 ml. of acetic acid is cooled to 15° and saturated with hydrogen chloride gas. The reaction mixture is allowed to warm to 25° and stirred for 23 hours. The solvent is removed in vacuo, the residue is distilled twice and the fraction boiling at 170°–190° (0.02 mm.) is collected and chromatographed on silica gel with benzene as eluant. The nonpolar fractions are rechromatographed on a silver nitrate impregnated silica gel "dry-column" with 18:1:1 cyclohexaneacetic acid-ether to give a mixture which is separated by distillation to give the title compounds, b.p. 180° (0.005 mm.), tetrahydro xanthene; b.p. 190° (0.003 mm.), aromatic xanthene.

B. A solution of 26.2 g. of 5-(1,2-dimethylheptyl)-resorcinol and 16.5 g. of 2-acetylcyclohexanone in 150 ml. of acetic acid is cooled to 15° and saturated with hydrogen chloride gas. The mixture is allowed to warm to 25°, stirred for 48 hours and then quenched by pouring into 500 ml. of methanol at 0° and adding 40 g. of sodium bicarbonate to the methanol solution. Sodium cyanoborohydride is then added to the reaction mixture until the bright orange color is dissipated. The solution is concentrated in vacuo, water is added to the residue and the aqueous mixture is extracted with ether. The extract is washed with water and 5% aqueous sodium bicarbonate, dried ($MgSO_4$) and concentrated to give a residue which is chromatographed on silica. The less polar fraction is collected and dissolved in 150 ml. of pyridine. Acetic anhydride (64 g.) is added and the solution is refluxed 10 minutes then allowed to stir at 25° for 18 hours. The mixture is concentrated in vacuo, the residue is dissolved in hexane and the hexane solution is washed with water, dilute hydrochloric acid and water, dried ($Na_2SO_4$) and concentrated to give a residue which is chromatographed on silica with 1:1 methylene chloride-petroleum ether to give 1-acetoxy-3-(1,2-dimethylheptyl)-5,6,7,8-tetrahydro-9-methylxanthene.

1-Acetoxy-3-(1,2-dimethylheptyl)-5,6,7,8-tetrahydro-9-methylxanthene is refluxed with potassium carbonate in 100 ml. of 15% aqueous methanol for 15 minutes. The reaction mixture is diluted with cold water and extracted with hexane. The organic phase is washed with water, dried ($Na_2SO_4$) and concentrated in vacuo to give a residue which, upon distillation, gives 3-(1,2-dimethylheptyl)-5,6,7,8,-tetrahydro-1-hydroxy-9-methylxanthene.

EXAMPLE 4

3-(1,2-Dimethylheptyl)-5,6,7,8-tetrahydro-1-hydroxyxanthene

The title compound is prepared by substitution of an equivalent amount of 2-formylcyclohexanone in the procedure of Example 1 for 2-acetyl-5-methylcyclohexanone.

EXAMPLE 5

When an equivalent amount of a cyclohexanone listed below:
2-acetyl-3-methylcyclohexanone
2-propionylcyclohexanone
2-methyl-6-propionylcyclohexanone
3-methyl-2-propionylcyclohexanone
4-methyl-2-propionylcyclohexanone
is used as a starting material in place of 2-acetyl-5-methylcyclohexanone in the procedure of Example 1, the following compounds of this invention are obtained:
3-(1,2-dimethylheptyl)-5,6,7,8-tetrahydro-1-hydroxy-8,9-dimethylxanthene
3-(1,2-dimethylheptyl)-9-ethyl-5,6,7,8-tetrahydro-1-hydroxyxanthene
3-(1,2-dimethylheptyl)-9-ethyl-5,6,7,8-tetrahydro-1-hydroxy-5-methylxanthene
3-(1,2-dimethylheptyl)-9-ethyl-5,6,7,8-tetrahydro-1-hydroxy-8-methylxanthene
3-(1,2-dimethylheptyl)-9-ethyl-5,6,7,8-tetrahydro-1-hydroxy-7-methylxanthene.

EXAMPLE 6

3-(1,2-Dimethylheptyl)-6-ethyl-5,6,7,8-tetrahydro-1-hydroxy-9-methylxanthene

Pyrrolidine (71.0 g.) is added to a solution of 12.6 g. of 3-ethylcyclohexanone in 12.6 ml. of benzene and the mixture is refluxed for eight hours with azeotropic removal of water. The mixture is cooled (ice bath) and 10.1 g. of diethylamine followed by 10.0 g. of acetyl chloride are added dropwise. The resulting mixture is refluxed for two hours then cooled and quenched by addition of 15.0 ml. of concentrated hydrochloric acid. The reaction mixture is refluxed an additional 15 minutes, cooled and diluted with water. The mixture is extracted with ether and the ethereal phase is washed with water, dried (MgSO$_4$) and concentrated in vacuo to give a residue which, upon distillation in vacuo, gives 2-acetyl-5-ethylcyclohexanone.

Substitution of an equivalent amount of 2-acetyl-5-ethylcyclohexanone in the procedure of Example 1 for 2-acetyl-5-methylcyclohexanone gives the title compound.

EXAMPLE 7

Reaction of 2-acetyl-5-methylcyclohexanone with 5-(1-methylheptyl)resorcinol according to the procedure of Example 1 gives 5,6,7,8-tetrahydro-1-hydroxy-6,9-dimethyl-3-(1-methylheptyl)xanthene.

In like manner, 5,6,7,8-tetrahydro-1-hydroxy-6,9-dimethyl-3-(1-methylhexyl)xanthene is prepared when 5-(1-methylhexyl)resorcinol is used as a starting material in the procedure of Example 1 in place of 5-(1,2-dimethylheptyl)resorcinol.

EXAMPLE 8

3-(1,2-Dimethyldecyl)-5,6,7,8-tetrahydro-1-hydroxy-6,9-dimethylxanthene

To the Grignard reagent prepared from 13.3 g. of magnesium turnings and 123.9 g. of 2-bromodecane in anhydrous ether, under nitrogen, is added with stirring a solution of 50.5 g. of 3,5-dimethoxyacetophenone [J. Prakt. Chem. 107:104 (1924)] in 200 ml. of anhydrous tetrahydrofuran. After refluxing for 12 hours the mixture is quenched with 300 ml. of saturated aqueous ammonium chloride and extracted with ether. The extracts are washed with water, dried (MgSO$_4$) and the solvent is removed to give 5-(1,2-dimethyl-1-hydroxydecyl)resorcinol dimethyl ether.

Dehydration by distillation from a few drops of 20% aqueous sulfuric acid gives a mixture of 5-(1,2-dimethyldec-1-enyl)resorcinol dimethyl ether and 5-(1-methylenyl-2-methyldecyl)resorcinol dimethyl ether which is hydrogenated over 10% palladium-on-carbon in absolute ethanol at 50 p.s.i. and 25° to give 5-(1,2-dimethyldecyl)-resorcinol dimethyl ether.

A solution of 30.6 g. of 5-(1,2-dimethyldecyl)-resorcinol dimethyl ether in 350 ml. of glacial acetic acid and 150 ml. of 48% hydrogen bromide is refluxed eight hours, then stirred at 25° for 12 hours. The reaction mixture is diluted with water and extracted three times with ether. The combined extracts are washed with saturated aqueous sodium bisulfite and saturated aqueous sodium bicarbonate, dried (MgSO$_4$), concentrated and distilled to give 5-(1,2-dimethyldecyl)resorcinol.

Substitution of 5-(1,2-dimethyldecyl)resorcinol in the procedure of Example 1 for 5-(1,2-dimethylheptyl)-resorcinol gives the title compound.

EXAMPLE 9

5,6,7,8-Tetrahydro-1-hydroxy-6,9-dimethyl-3-(1,1,2-trimethylheptyl)xanthene

To 0.2 mol. of methyl magnesium bromide (2N in tetrahydrofuran-benzene), under nitrogen, is added 55.6 g. of 2-(3,5-dimethoxyphenyl)-2-methyloct-3-one [J. Amer. Chem. Soc. 70:664 (1948); Helv. Chim. Acta 52:116 (1969)] in tetrahydrofuran. After refluxing for 12 hours the mixture is quenched with saturated aqueous ammonium chloride and extracted with ether. The extracts are washed with water, dried (MgSO$_4$) and the solvent is removed to give 5-(2-hydroxy-1,1,2-trimethylheptyl)resorcinol dimethyl ether as an oil. A solution of 5.9 g. of the carbinol in ether is allowed to react over a six hour period with a suspension of 0.8 g. of metallic potassium in 60 ml. of ether. Carbon disulfide (1.5 g.) is added and the mixture is stirred for 30 minutes, then 2.8 g. of methyl iodide is added and the reaction mixture is refluxed for six hours and left at 25° for 12 hours. The mixture is filtered and the filtrate is concentrated and distilled in vacuo. The distillate is dissolved in ethanol, refluxed with Raney nickel and redistilled to give a mixture of 5-(1,1,2-trimethylhept-2-enyl)resorcinol dimethyl ether and 5-(1,1-dimethyl-2-methylenylheptyl)resorcinol dimethyl ether. Removal of the protective groups and hydrogenation is accomplished as described in Example 8 to give 5-(1,1,2-trimethylheptyl)resorcinol.

Reaction of 5-(1,1,2-trimethylheptyl)resorcinol with 2-acetyl-5-methylcyclohexanone as described in Example 1 gives the title compound.

EXAMPLE 10

3-(1-Ethyl-2-methylheptyl)-5,6,7,8-tetrahydro-1-hydroxy-6,9-dimethylxanthene

Substitution of equivalent amounts of 3,5-dimethoxyphenyl ethyl ketone and 3-bromoheptane in the procedure of Example 8 for 3,5-dimethoxyacetophenone and 2-bromodecane followed by dehydration, hydrogenation, and removal of the protective groups as described gives 5-(1-ethyl-2-methylheptyl)resorcinol.

Condensation of 5-(1-ethyl-2-methylheptyl)resorcinol and 2-acetyl-5-methylcyclohexanone as described in Example 1 gives the title compound.

EXAMPLE 11

3-(1,2-Diethylheptyl)-5,6,7,8-tetrahydro-1-hydroxy-6,9-dimethylxanthene

Substitution of equivalent amounts of 3,5-dimethoxyphenyl ethyl ketone and 3-bromooctane in the procedure of Example 8 for 3,5-dimethoxyacetophenone and 2-bromodecane followed by dehydration, hydrogenation and removal of the protective groups as described gives 5-(1,2-diethylheptyl)resorcinol.

Condensation of 5-(1,2-diethylheptyl)resorcinol and 2-acetyl-5-methylcyclohexanone as described in the procedure of Example 1 gives the title compound.

EXAMPLE 12

When 2-bromononane is used as a starting material in place of 2-bromodecane in the procedure of Example 8, 5-(1,2-dimethylnonyl)resorcinol is obtained as the product.

Reaction of 5-(1,2-dimethylnonyl)resorcinol and 2-acetyl-5-methylcyclohexanone as described in Example 1 gives 3-(1,2-dimethylnonyl)-5,6,7,8-tetrahydro-1-hydroxy-6,9-dimethylxanthene.

Similarly, use of 2-bromooctane as a starting material in place of 2-bromodecane in the procedure of Example 8 gives 5-(1,2-dimethyloctyl)resorcinol as the product.

Substitution of 5-(1,2-dimethyloctyl)resorcinol in the procedure of Example 1 for 5-(1,2-dimethylheptyl)-resorcinol gives 3-(1,2-dimethyloctyl)-5,6,7,8-tetrahydro-1-hydroxy-6,9-dimethylxanthene.

EXAMPLE 13

3-(1,2-Dimethylheptyl)-5a,5,6,7,8,8a-hexahydro-1-hydroxy-6,9-dimethylxanthene

A solution of 2.5 g. of 3-(1,2-dimethylheptyl)-5,6,7,8-tetrahydro-1-hydroxy-6,9-dimethylxanthene in 25 ml. of glacial acetic acid is hydrogenated over platinum on silica gel at 50 p.s.i. until one equivalent of hydrogen is absorbed. The suspension is then filtered, the filtrate is poured into water and the aqueous solution is extracted with ether. The ethereal phase is washed with water, aqueous sodium bicarbonate and saturated aqueous sodium chloride solution, dried ($MgSO_4$) and concentrated to give a residue which is distilled to give the title compound

EXAMPLE 14

5,6,7,8-Tetrahydro-1-hydroxy-3-(2-methylheptyl)-6,9-dimethylxanthene

By use of 3,5-dimethoxybenzaldehyde and 2-bromoheptane as starting materials in the procedure of Example 8 in place of 3,5-dimethoxyacetophenone and 2-bromodecane, 5-(2-methylheptyl)resorcinol is prepared.

When 5-(2-methylheptyl)resorcinol is reacted with 2-acetyl-5-methylcyclohexanone as described in Example 1 the title compound is obtained.

Example 15

1-Acetoxy-3-(1,2-dimethylheptyl)-5,6,7,8-tetrahydro-6,9-dimethylxanthene

To a solution of 1.2 g. of 3-(1,2-dimethylheptyl)-5,6,7,8-tetrahydro-1-hydroxy-6,9-dimethylxanthene in 20 ml. of dry pyridine is added 8.0 g. of acetic anhydride. The solution is stirred at 25° for 24 hours, then concentrated in vacuo. The residue is dissolved in water and extracted with hexane. The extract is washed with water until neutral, then dried and evaporated to give the title compound.

EXAMPLE 16

By the procedure of Example 15, using propionic anhydride in place of acetic anhydride, the product is 3-(1,2-dimethylheptyl)-5,6,7,8-tetrahydro-6,9-dimethyl-1-propionyloxyxanthene.

Similarly, using n-butyric anhydride, the product is 1-n-butyryloxy-3-(1,2-dimethylheptyl)-5,6,7,8-tetrahydro-6,9-dimethylxanthene.

By the same procedure, using n-valeric anhydride, the product is 3-(1,2-dimethylheptyl)-5,6,7,8-tetrahydro-6,9-dimethyl-1-n-valeryloxyxanthene.

EXAMPLE 17

When an equivalent amount of 3-(1,2-dimethylheptyl)-5,6,7,8-tetrahydro-1-hydroxyxanthene is substituted in the procedure of Example 16 for 3-(1,2-dimethylheptyl)-5,6,7,8-tetrahydro-1-hydroxy-6,9-dimethylxanthene, 1-acetoxy-3-(1,2-dimethylheptyl)-5,6,7,8-tetrahydroxanthene is obtained.

Similarly, the 1-propionyl, 1-n-butyryl and 1-n-valeryl derivatives may be prepared.

What is claimed is:

1. A compound of the formula:

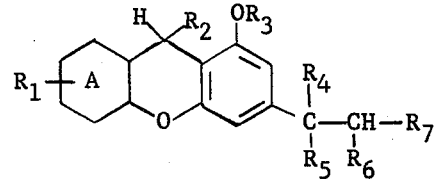

in which:
ring A is a benzene ring, a cyclohexane ring or a cyclohexene ring with the double bond at position 5a-8a;
$R_1$ is hydrogen, methyl or ethyl;
$R_2$ is hydrogen, methyl or ethyl;
$R_3$ is hydrogen or alkanoyl of from two to five carbon atoms;
$R_4$ is hydrogen, methyl or ethyl and $R_5$ and $R_6$ are hydrogen or methyl, at least one of $R_4$, $R_5$ and $R_6$ being other than hydrogen; and
$R_7$ is alkyl of from four to eight carbon atoms.

2. A compound as claimed in claim 1 where ring A is a benzene ring or a cyclohexene ring with the double bond at position 5a-8a.

3. A compound as claimed in claim 2 where $R_4$ is methyl and $R_5$ and $R_6$ are hydrogen or methyl.

4. A compound as claimed in claim 3 where $R_1$ is hydrogen or methyl in the 6-position, $R_2$ is hydrogen or methyl, $R_3$ is hydrogen or acetyl and $R_7$ is n-pentyl.

5. A compound as claimed in claim 4 being the compound 3-(1,2-dimethylheptyl)-5,6,7,8-tetrahydro-1-hydroxy-9-methylxanthene.

6. A compound as claimed in claim 4 being the compound 3-(1,2-dimethylheptyl)-1-hydroxy-6,9-dimethylxanthene.

7. A compound as claimed in claim 4 being the compound 3-(1,2-dimethylheptyl)-1-hydroxy-9-methylxanthene.

* * * * *